(12) United States Patent
Pelton

(10) Patent No.: US 6,824,560 B2
(45) Date of Patent: Nov. 30, 2004

(54) DOUBLE-BUTTED SUPERELASTIC NITINOL TUBING

(75) Inventor: Brian Lee Pelton, Menlo Park, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 8 days.

(21) Appl. No.: 09/881,377

(22) Filed: Jun. 13, 2001

(65) Prior Publication Data

US 2004/0015226 A1 Jan. 22, 2004

(51) Int. Cl.⁷ .................................................. A61F 2/06
(52) U.S. Cl. ...................... 623/1.15; 623/1.113; 600/36
(58) Field of Search .............................. 623/1.19, 1.15, 623/1.3, 1.31, 1.16, 1.35, 1.113; 600/36

(56) References Cited

U.S. PATENT DOCUMENTS

| | | |
|---|---|---|
| 3,868,956 A | 3/1975 | Alfidi et al. |
| 4,512,338 A | 4/1985 | Balko et al. |
| 4,553,545 A | 11/1985 | Maass et al. |
| 4,616,500 A | 10/1986 | Alexoff |
| 4,665,906 A | 5/1987 | Jervis |
| 4,733,665 A | 3/1988 | Palmaz |
| 4,762,128 A | 8/1988 | Rosenbluth |
| 4,800,882 A | 1/1989 | Gianturco |
| 4,856,516 A | 8/1989 | Hillstead |
| 4,886,062 A | 12/1989 | Wiktor |
| 5,067,957 A | 11/1991 | Jervis |
| 5,190,546 A | 3/1993 | Jervis |
| 5,421,955 A | 6/1995 | Lau |
| 5,486,183 A | 1/1996 | Middleman et al. |
| 5,509,923 A | 4/1996 | Middleman et al. |
| 5,569,295 A | 10/1996 | Lam |
| 5,597,378 A | 1/1997 | Jervis |
| 5,632,746 A | 5/1997 | Middleman et al. |
| 5,709,021 A | 1/1998 | DiCello et al. |
| 5,720,754 A | 2/1998 | Middleman et al. |
| 5,759,192 A | * 6/1998 | Saunders |
| 5,843,244 A | * 12/1998 | Pelton et al. |
| 5,876,448 A | * 3/1999 | Thompson et al. |
| 5,885,381 A | 3/1999 | Mitose et al. |
| 6,004,330 A | 12/1999 | Middleman et al. |
| 6,027,526 A | * 2/2000 | Limon et al. |
| 6,131,266 A | 10/2000 | Saunders |
| 6,190,406 B1 | 2/2001 | Duerig et al. |
| 6,200,335 B1 | * 3/2001 | Igaki |
| 6,453,536 B1 | 9/2002 | Müller et al. |

FOREIGN PATENT DOCUMENTS

EP          0 873 734          10/1998

OTHER PUBLICATIONS

Duerig, T.W. et al., Linear Superelasticity in Cold–Worked Ni–Ti, *Engineering Aspects of Shape Memory Alloys*, pp. 414–419 (1990).

* cited by examiner

*Primary Examiner*—Nicholas D. Lucchesi
*Assistant Examiner*—Lalita M Hamilton
(74) *Attorney, Agent, or Firm*—Fulwider Patton Lee & Utecht, LLP

(57) ABSTRACT

A medical device such as a stent made from single or double-butted tubing is disclosed. The butted tubing may be made from stainless steel or a nickel-titanium (nitinol) alloy. The butted tubing is created by thinning the material in between the ends of the tube through machining, drawing, cold working, laser cutting, or chemical etching. A strut pattern for a stent is laser cut into the butted tubing. The strut pattern for the stent includes rings connected by links. The end rings of the stent coincide with the double-butted ends of the tubing thereby increasing the hoop strength of those end rings.

24 Claims, 2 Drawing Sheets

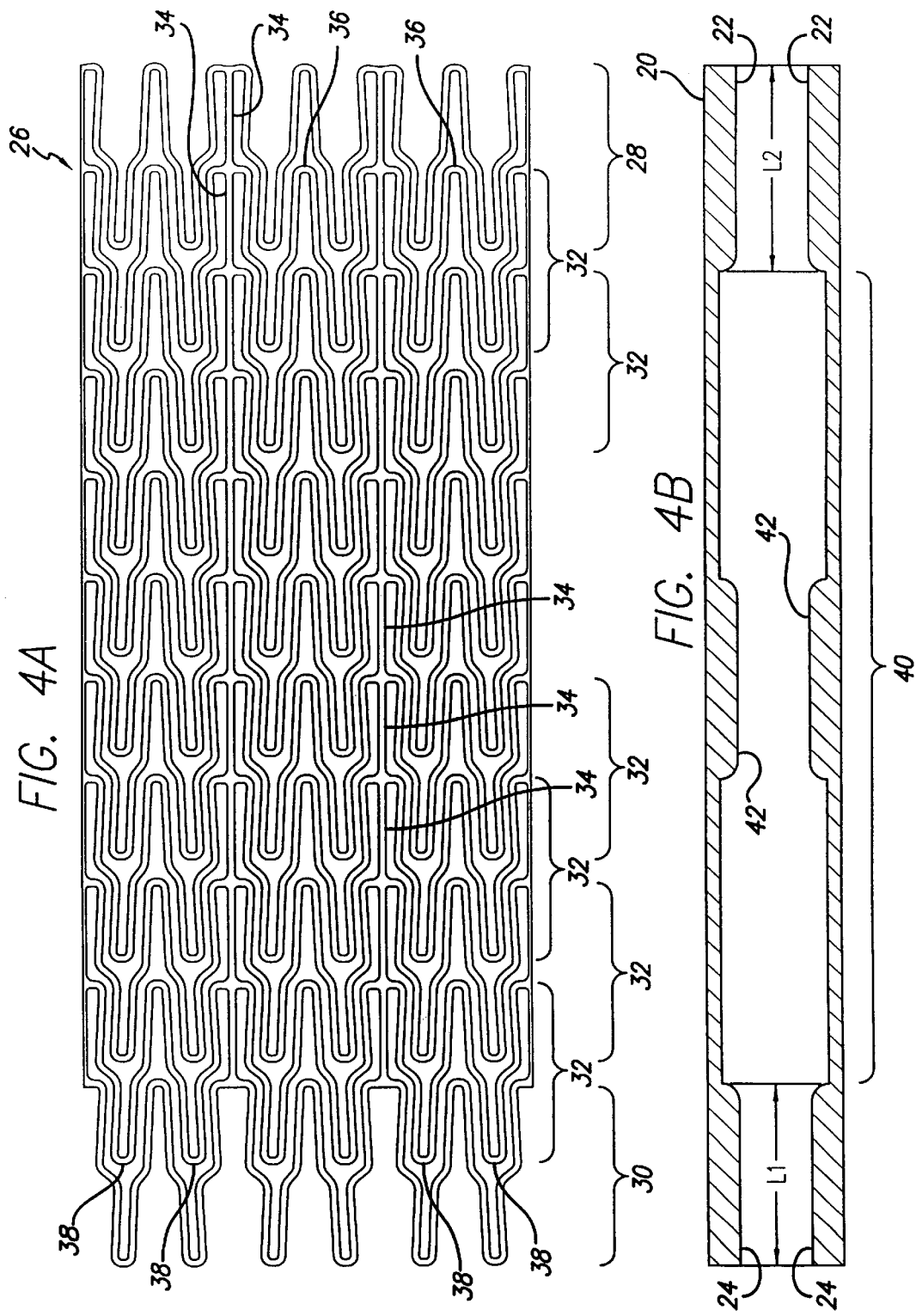

DOUBLE-BUTTED SUPERELASTIC NITINOL TUBING

BACKGROUND OF THE INVENTION

The present invention relates generally to the application of nickel-titanium alloys to medical devices. More precisely, the present invention is directed to creating double-butted tubing made of nickel-titanium alloys for use in medical devices.

Several interventional treatment modalities are presently used for heart disease, including balloon and laser angioplasty, atherectomy, and by-pass surgery. In typical coronary balloon angioplasty procedures, a guiding catheter having a distal tip is percutaneously introduced through the femoral artery into the cardiovascular system of a patient using a conventional Seldinger technique and advanced within the cardiovascular system until the distal tip of the guiding catheter is seated at the ostium of the coronary arteries. A guide wire is positioned within an inner lumen of a dilatation catheter and then both are advanced through the guiding catheter to the distal end thereof.

The guide wire is first advanced out of the distal end of the guiding catheter into the patient's coronary vasculature until the distal end of the guide wire crosses a lesion to be dilated, then the dilatation catheter having an inflatable balloon on the distal portion thereof is advanced into the patient's coronary anatomy over the previously introduced guide wire until the balloon of the dilatation catheter is properly positioned across the lesion.

Once in position across the lesion, the balloon is inflated to compress the plaque of the lesion against the inside of the artery wall and to otherwise expand the inner lumen of the artery. The balloon is then deflated so that blood flow can be resumed through the dilated artery and the dilatation catheter can be removed therefrom.

One problem that can occur during balloon angioplasty procedures is the formation of intimal flaps which can collapse and occlude the artery when the balloon is deflated at the end of the angioplasty procedure. Another problem characteristic of balloon angioplasty procedures is the large number of patients who are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

A focus of recent developmental work in the treatment of heart disease is an endoprosthetic device referred to as a stent. A stent is a generally cylindrically shaped intravascular device that is implanted in a diseased artery to hold it open. The device is thus used to maintain the patency of a blood vessel immediately after intravascular treatments, and further reduces the likelihood of restenosis. In some circumstances, a stent can be used as the primary treatment device where it is expanded to dilate a stenosis and then left in place. Further details of stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); U.S. Pat. No. 4,886,062 (Wiktor); U.S. Pat. No. 5,421,955 (Lau); and U.S. Pat. No. 5,569,295 (Lam), which are hereby incorporated by reference.

One method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway.

A limitation of some prior art stents, especially those of the balloon expandable type, is that they are stiff and inflexible. Often, the expandable type stents are formed from stainless steel alloys and are constructed so that they are expanded beyond their elastic limit. Such stents are permanently deformed beyond their elastic limits in order to hold open a body lumen and to maintain the patency of the body lumen. By the same token, since the material is stressed beyond its elastic limit into the plastic region, the material becomes stiff and inflexible.

There are several commercially available stents that are widely used and generally implanted in the coronary arteries after a PTCA (Percutaneous Transluminal Coronary Angioplasty) procedure, described earlier. Stents are also implanted in vessels that are closer to the surface of the body, such as in the carotid arteries in the neck or in peripheral arteries and veins in the leg. Because these stents are implanted so close to the surface of the body, they are particularly vulnerable to impact forces that can partially or completely collapse the stent and thereby block fluid flow in the vessel. Under certain conditions, muscle contractions might cause the stent to partially or totally collapse. Since balloon expandable stents are plastically deformed, once collapsed or crushed, they remain so, permanently blocking the vessel. These expandable stents might therefore pose an undesirable condition to the patient.

Such important applications as mentioned above have prompted stent designers to use superelastic or shape memory alloys in their stent to exploit the materials' properties. Typically, the superelastic or shape memory alloy of choice is nickel-titanium, also known as nitinol. A nitinol stent is self-expanding and is highly resilient. As a result, a nitinol stent is not commonly deformed plastically when deployed, and remains highly resilient inside the body lumen. Because of this resilience, the self-expanding nitinol stent can encounter a deforming impact yet return to its initial shape. The chance of a permanent collapse of the self-expanding nitinol stent due to an impact force is thus minimized. An example of such shape memory alloy stents is disclosed in, for example, European Patent Application Publication No. EP0873734A2, entitled "Shape Memory Alloy Stent," which is hereby incorporated by reference.

The evolution of superelastic and shape memory alloy stents progressed to use of ternary elements in combination with nickel-titanium alloys to obtain specific material properties. As a general proposition, there have been attempts at adding a ternary element to nickel-titanium alloys as disclosed in, for instance, U.S. Pat. No. 5,885,381 to Mitose et al., which is hereby incorporated by reference.

Nickel-titanium alloys are frequently chosen for use in self-expanding stents due to their highly elastic behavior. Near equi-atomic binary nickel-titanium alloys are known to exhibit "pseudoelastic" behavior when given certain cold working processes or cold working and heat treatment processes following hot working. Generally speaking, "pseudoelasticity" is the capacity of the nickel-titanium alloy to undergo large elastic strains on the order of 8 percent or more when stressed and to substantially fully recover all strain upon removal of the stress. Substantially full recovery is typically understood to be less than 0.5 percent unrecovered strain, also known as permanent set or amnesia.

Pseudoelasticity can be further divided into two subcategories: "linear" pseudoelasticity and "non-linear" pseudoelasticity. "Non-linear" pseudoelasticity is sometimes used by those in the industry synonymously with "superelasticity."

Linear pseudoelasticity results from cold working only. Non-linear pseudoelasticity results from cold working and subsequent heat treatment. Non-linear pseudoelasticity, in its idealized state, exhibits a relatively flat loading plateau in which a large amount of recoverable strain is possible with very little increase in stress. This flat plateau can be seen in the stress-strain hysteresis curve of the alloy. Linear pseudoelasticity exhibits no such flat plateau. Non-linear pseudoelasticity is known to occur due to a reversible phase transformation from austenite to martensite, the latter more precisely called "stress-induced martensite" (SIM). Linear pseudoelasticity has no such phase transformation associated with it. Further discussions of linear pseudoelasticity can be found in, for example, T. W. Duerig, et al., "Linear Superelasticity in Cold-Worked Ni—Ti," *Engineering Aspects of Shape Memory Alloys*, pp. 414–19 (1990).

Binary nickel-titanium alloys have been used in the medical field. Many medical device related applications exploit the non-linear pseudoelastic capabilities of nitinol. Examples include: U.S. Pat. Nos. 4,665,906; 5,067,957; 5,190,546; and 5,597,378 (Jervis); and U.S. Pat. Nos. 5,509,923; 5,486,183; 5,632,746; 5,720,754; and 6,004,330 (Middleman et al.), whose contents are hereby incorporated by reference.

One specific problem with self-expanding stents is the tendency for the proximal and distal end rings to collapse. This collapse compromises the mean lumen diameter (MLD). The collapse therefore detrimentally affects the actual versus expected deployment diameter of the stent. Also, collapsed end rings means that the scaffolding capability of the stent at its ends are diminished. Hence, what has been needed and heretofore unavailable in the prior art is a tubular shaped medical device that exploits the benefits of superelastic materials and structurally compensates for the inherently weak ends of a tubular structure.

SUMMARY OF THE INVENTION

The present invention in a preferred embodiment is directed to a stent for use in a body lumen, comprising a body having a tubular shape with opposite ends wherein at least one of the ends is butted; and a strut pattern formed from the tubular shape wherein the strut pattern includes a plurality of cylindrical rings generally coaxially aligned and interconnected by connecting links. The present invention stent is preferably made from a tubular shape that is butted at one or both ends, and each of the butted ends optionally coincides with a ring of the finished stent.

The present invention stent has a given wall thickness and the butted ends, as the term suggests, have a greater wall thickness than the wall therebetween. The thicker ends may be fashioned from a variety of tubing manufacturing processes, such as machining, cold working or drawing to thin the wall in between the ends, etc.

The preferred embodiment stent is further made from a nickel-titanium alloy. The nickel-titanium alloy, in a preferred embodiment, has a phase transformation temperature above 37 degrees C. The nickel-titanium alloy may be optionally cold-worked, heat treated, and may optionally include a ternary element to obtain desired engineering properties.

The resulting preferred embodiment self-expanding stent has all of the beneficial attributes of a superelastic medical device, and further exhibits great hoop strength especially for the rings that coincide with the double-butted ends. The risk of collapse at the stent ends therefore is dramatically reduced.

Other features and advantages of the present invention will become more apparent from the following detailed description of the invention when taken in conjunction with the accompanying exemplary drawings.

BRIEF DESCRIPTION OF THE DRAWINGS

FIG. 4a is a plan view of a strut pattern of the present invention stent wherein the pattern has been unrolled from a tube into a plane to illustrate the design.

FIG. 4b is a cross-sectional view of a finished double-butted tubing wherein the double-butted ends coincide with the end rings of the strut pattern shown in FIG. 4a.

DETAILED DESCRIPTION OF THE PREFERRED EMBODIMENTS

Figure 1:
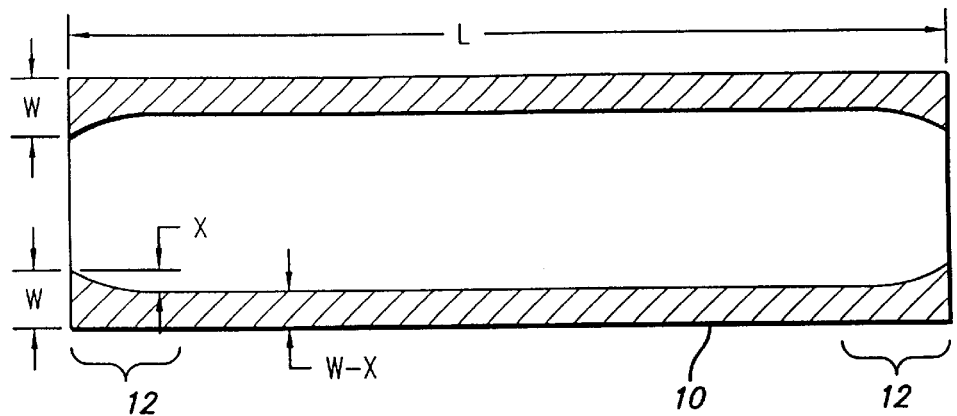
FIG. 1 is a cross-sectional view of a tube having double-butted ends for use in fabricating the present invention stent.

The present invention is generally directed to a stent for use in a body lumen, wherein the stent is fabricated from a tubular form having a single butted end or double-butted ends. The single or double-butted ends serve to reinforce the proximal and distal ends of the stent where hoop strength is sometimes unsatisfactory. Although the present invention is applicable to and contemplates numerous tubular shaped medical devices, for the sake of illustration, the following detail description focuses on an exemplary embodiment involving a stent.

Double-butted tubing is generally known for its application in the bicycling industry. In general, frames used in bicycles are made from metal tubing that is either seamed or seamless. Seamed tubing is inexpensive and used in bicycles to minimize cost. A seamed tube begins as a flat sheet of metal, such a steel, and is rolled into a tube. The seam that extends along the length of the tube is then welded. By comparison, seamless tubing for bicycles is made from higher quality metals. A seamless tube starts as a solid bar of steel. The metal bar stock is heated to red hot intensity and drawn over a pointed steel bar known as a mandrel. The tubing is next drawn through a series of dies until its outside diameter or wall thickness has met the design criteria.

High quality seamless tubing for use in bicycles often undergo yet an additional step. Specifically, the tubing is butted to make the wall thickness at the ends of the tubing thicker than the middle while the outside diameter remains constant. Bicycle designers desire double-butted tubing because it strengthens the area of the tubing where stress is greatest while conserving weight for the tubing in areas that encounter less stress. Consequently, the ends of the tubing are double-butted because the ends are joined to other parts of the frame where high loads are seen. By only butting the ends, the thin wall of the tubing in the middle section keeps the overall weight of the tubing low.

Single or double-butted bicycle tubing is manufactured through several processes depending on the method used to butt the tube and whether the tube is seamless or seamed. Butting the tube is created by either a mandrel press process or by moving plug cold drawing. In the mandrel press process, the tubing is pushed through a die while simultaneously sinking the tubing down onto a mandrel. The mandrel has a smaller diameter at the ends than in the middle thus creating a taper at each end. The die determines the outside diameter and profile of the tube while the mandrel sets the inside diameter. Having those two dimensions set, the wall thickness of the tubing is established. After passing through the die, the mandrel is trapped inside the tube. The tube has a conventional double-butted geometry in which the tube wall is thicker at the ends (where the mandrel diameter is smaller) and the tube wall in the middle area is thinner (where the mandrel diameter is larger).

The mandrel is removed during "reeling" the tube between angled rotating rollers. The reeling process involves withdrawing the mandrel from the tubing. As this occurs, the larger diameter middle section of the mandrel creates a bulge in the tube diameter as it slides out through one end with the greater wall thickness. This increase in the tube diameter has negligible effect on the wall thickness. Next the increased diameter of the tubing is resized to match the smaller diameter of the mid-section by pushing the tube through a die. The operation is performed on a machine called a reeler, which spins the tube between inclined rollers that increase the tube's diameter just enough to allow removal of the mandrel.

The alternative method to making single or double-butted tubing for the bicycle industry is known as moving plug cold drawing. In this process, a die is used to control the outside diameter of the tube, and the internal diameter is controlled by a plug. The taper rate of the plug and die are arranged so that if the plug is moved or advanced through the die as the tubing also passes through the die, the wall thickness decreases. Essentially, the plug pinches the tubing wall between it and the die. On the other hand, if the plug is not advanced as far through the die, then the wall thickness of the tubing as it passes through that die increases. Therefore, by controlling the movement of the plug relative to the die as the tubing is drawn through the die, a butted tube is formed. This process of moving plug butting entails only a single manufacturing operation and is more efficient and cost effective than applying a mandrel press process. However, the mandrel press process oftentimes produces tubing of greater precision in setting the wall thickness of the butted ends and the longitudinal dimensions of the butted ends. Lastly, either process can be used to create butted ends on seamless or welded, seamed tubing FIG. 1 is a cross-sectional view of a double-butted tubing 10 used to fabricate the preferred embodiment of the present invention stent. A single-butted tubing (not shown) appears identical to the tubing of FIG. 1 except that one of the ends does not have the large wall thickness created by the butting 22, 24. The double-butted tubing 10 has a length L, wherein W represents the tubing wall thickness at the double-butted ends 12 and X represents the amount of wall thickness reduction in the middle section in between the double-butted ends 12. This area has a wall thickness of W-X.

Figure 2:
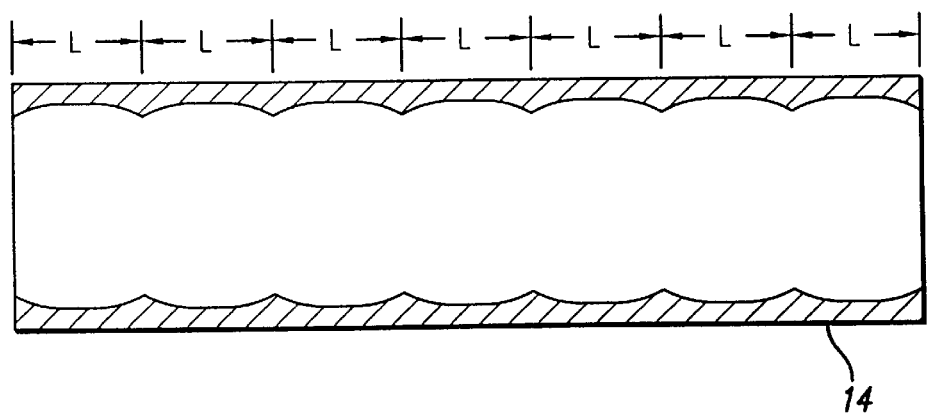
FIG. 2 is a cross-sectional view of a length of stock tubing from which many pieces of double-butted tubes may be cut.

In order to conserve material, the finished length L can be cut from a length of stock tubing having multiple butted ends as shown in the cross-sectional view of FIG. 2. In the exemplary illustration of FIG. 2, the stock tubing 14 has a length of 7L, which includes seven sections of double-butted tubing 10 having a length L. From this stock tubing 14, seven double-butted tubes 10 can be cut from which seven stents can be fabricated.

Figure 3:
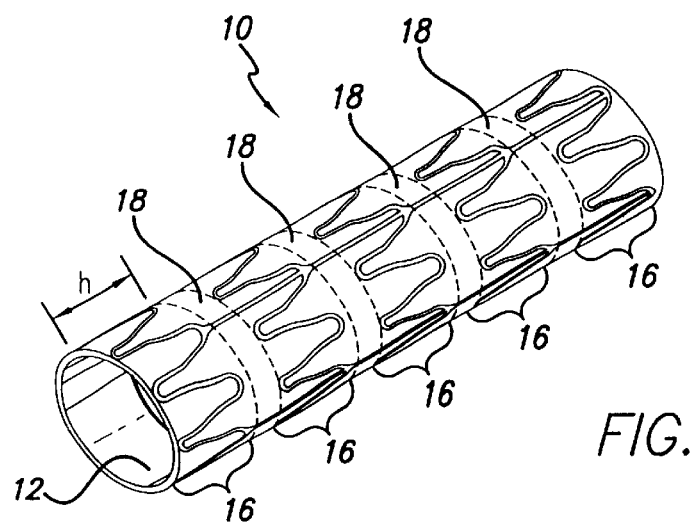
FIG. 3 is a perspective view of a body having a tubular shape wherein a strut pattern has been superimposed onto the exterior surface prior to formation of the strut pattern therein. The strut pattern is made up of a plurality of cylindrical rings and connecting links.

FIG. 3 is a perspective view of the tubing shown in FIG. 1 wherein a strut pattern for a desired stent has been superimposed on the outside surface. The strut pattern can be of any desired tubular shape, design, or form, but has been chosen for this preferred embodiment to include a plurality of rings 16 arranged in a generally coaxial relationship. Pairs of adjacent rings 16 are interconnected by a radial arrangement of links 18 that extend axially generally parallel to the longitudinal axis of the tubing 10. In the exemplary embodiment shown, the links 18 are optionally aligned or co-linear, but of course, they may be staggered so that they are not aligned along the length of the tubing 10. Also, in the embodiment shown in FIG. 3, the links 18 are evenly spaced 120 degrees radially apart, but it is understood that other radial spacings such as 15, 30, 45, 60 degrees, etc., either evenly or unevenly spaced apart, are contemplated.

Furthermore, the number of the rings 16 used and the number and locations of the links 18 used to join the rings can be varied as needed. The dimensional proportions of the rings (diameter, height, thickness, etc.) and the links (length, width, thickness, etc.) can be varied as well. In fact, the numbers, physical dimensions, and spacings of the rings and links can be non-uniform.

In the preferred embodiment shown in FIG. 3, the butted end 12 optionally coincides with a ring 16 and has a length coextensive with the height h of the ring 16. The tubing 10 shown includes butting at both ends, but of course the butting can be omitted from one end. Furthermore, the wall thickness W of the butted ends 12 can vary between the two ends as needed. Naturally, the thicker the wall thickness at the butted end, the greater the hoop strength at that end in the finished stent.

For typical use in coronary arteries, the balloon expandable stent diameter is very small so the tubing from which it is made must necessarily also have a small diameter. The stent has an outside diameter on the order of, for example, about 0.06 inch in the unexpanded condition, equivalent to the tubing from which the stent is made, and can be further expanded by a balloon catheter to an outer diameter of about 0.1 inch or more. The wall thickness of the tubing is usually about 0.003 inch. For the category of self-expanding stents for use in the internal carotid artery, for example, the unconstrained stent diameters range from 5 to 10 mm with typical stent lengths of 20, 30, or 40 mm. For these self-expanding stents, the unconstrained stent diameter corresponds to the tubing diameter. The wall thickness is typically in the range of 0.0045 inch.

The stock tubing is made from 316L stainless steel, nickel-titanium alloys, or the like. The tubing can be single or double-butted through a variety of processes including the mandrel press or moving plug cold drawing as described above. Other processes include material removal through machining to reduce the wall thickness between the butted ends, or using pinch rollers to cold roll the wall thickness down to a smaller size.

Unlike bicycle tubing which is on the order of usually 1 inch or more in diameter, the present invention uses fairly small diameter tubing on the order of 5 to 10 mm. Because of this small size, still other methods of machining may be employed to create the butted ends. For example, electric discharge machining (EDM), laser beam machining, chemical etching, or a combination of processes are contemplated to cut such small work pieces precisely and repetitively for large production batches.

Once the butted tubing is available, the next step is to transfer a strut pattern to the tubing. The strut pattern may be transferred to the tubing through a combination of masking and chemical etching, or through laser cutting by use of computer numerical control (CNC) equipment. Preferably, the latter is employed to create the desired strut pattern similar to that shown in FIG. 3. Essentially, the strut pattern is programmed into a computer which then guides the laser beam along the work piece to cut the pattern from the stock tubing. As shown in FIG. 3, the preferred embodiment pattern has rings 16 that coincide with the location of the butted ends 12. U.S. Pat. No. 6,131,266 (Saunders), whose contents are hereby incorporated by reference, provides a detailed explanation of the methods and apparatus used for direct laser cutting of metal stents. U.S. Pat. No. 6,066,168 (Lau et al.), whose contents are hereby incorporated by reference, also provides details of stent fabrication.

FIG. 4a is a plan view of a strut pattern cut into a tube, wherein the tube has been unrolled and flattened into a sheet to illustrate the strut pattern. FIG. 4b is a cross-sectional view of a double-butted tubing 20 having double-butted ends 22, 24. The plan view of the strut pattern 26 shown in FIG. 4a is purposely aligned with the cross-sectional view of the double-butted tubing 20 shown in FIG. 4b. From these views, it is clear that the butted ends 22, 24 coincide with the distal and proximal end rings 28, 30 of the stent strut pattern 26.

In the strut pattern shown in FIG. 4a, the rings 32 are "nested" so that the peaks or valleys of one ring 32 encroaches on the peak or valley, respectively, of the adjacent ring 32. Again, the rings 32 are interconnected by links 34. In the embodiment shown in FIG. 4a, the links 34 are optionally aligned along the length of the strut pattern 26 and are uniformly spread 120 degrees radially apart. Of course, other strut patterns are contemplated including those in which the links 34 are alternating, or not aligned and are spread at radial angles other than 120 degrees.

Because the rings 32 and end rings 28, 30 are nested, the butted ends 22, 24 coincide with the peaks 36 or valleys 38 of the rings 32 immediately adjacent to the end rings 28, 30 so that those peaks 36 and valleys 38 have a greater strut thickness than those struts in the mid-section 40 of the tube 20. In contrast, the embodiment shown in FIG. 3 does not have nested rings.

As shown in FIG. 4b, the butted ends 22, 24 do not have to have the same thickness, and may further have different longitudinal dimensions L1 and L2. The lengths L1, L2 of the butted ends 22, 24, depend upon the strut pattern and the desired amount of reinforcement needed at the ends of the stent.

It is also contemplated in an alternative embodiment to include optional butting in the mid-section 40 of the tubing 20 as shown in the cross-sectional view of FIG. 4b. Here, butting 42 is created through the same processes as used for creating butted ends 22, 24, but the butting 42 is located at the mid-section 40. The location of the butting 42 preferably coincides with a ring 32 thereby improving the hoop strength of the stent at that location. Such a stent having a high hoop strength in a mid-section thereof might be useful for plaque build-up at the common carotid artery, for example. In such an application, a butted ring at the mid-section of the stent engages the plaque at the bifurcation while one end of the stent extends into the internal carotid and the opposite end extends into the common carotid.

The present invention contemplates use of nickel-titanium alloys. As mentioned above, such materials are typically used to fabricate self-expanding stents. The present invention can be used with linear pseudoelastic or non-linear pseudoelastic (i.e., superelastic) nitinol alloys. Linear pseudoelastic nitinol generally has a higher slope or Young's Modulus than for non-linear pseudoelastic nitinol. Also, linear pseudoelastic nitinol does not contain any flat plateau stresses found in stress-strain curve for a non-linear pseudoelastic nitinol. This stands to reason since linear pseudoelastic nitinol remains in the martensitic phase throughout and does not undergo any phase change. Increasing stress begets a proportional increase in reversible strain, and a release of stress begets a proportional decrease in strain.

As mentioned above, the present invention medical device uses preferably a binary nickel-titanium alloy. In an alternative embodiment, however, the nickel-titanium may be alloyed with a ternary element such as palladium, platinum, chromium, iron, cobalt, vanadium, manganese, boron, copper, aluminum, tungsten, tantalum, rhodium, or zirconium. Furthermore, the binary non-linear pseudoelastic nickel-titanium alloy has a transformation temperature preferably set at or below approximately 37 degrees C. or the body temperature of a human. The transformation temperature is the temperature of a non-linear pseudoelastic nitinol alloy in which the transformation from materials to austenite is complete. It is usually measured by $A_f$, the austenite finish temperature, but the austenite start temperature ($A_s$), martensite start temperature ($M_s$), or martensite finish temperature ($M_f$) may also be used as the metric.

While the present invention has been illustrated and described herein in terms of a superelastic nickel-titanium alloy stent fashioned from double-butted tubing, it is apparent to those skilled in the art that the present invention can be used in other instances. Other modifications and improvements may be made without departing from the scope of the present invention.

What is claimed is:

1. A medical device for use in a body lumen, comprising:
    a body having a tubular shape with opposite ends, wherein at least one of the ends is butted with material built up radially inward creating a greater wall thickness at that location while maintaining a constant outside diameter along a length of the tubular shape;
    wherein the body includes a nickel-titanium alloy that deforms superelastically inside the body lumen; and
    a strut pattern formed from the tubular shape wherein the strut pattern includes a plurality of cylindrical rings generally coaxially aligned and interconnected by connecting links.

2. The medical device of claim 1, wherein both ends of the tubular shape are butted.

3. The medical device of claim 1, wherein the butted end coincides with a ring.

4. The medical device of claim 1, wherein the butted end is created by a material removal process selected from the group of processes consisting of: electric discharge machining, laser beam cutting, or chemical etching.

5. The medical device of claim 1, wherein the butted end does not coincide with a ring.

6. The medical device of claim 1, wherein the body includes butting at a mid-section thereof.

7. The medical device of claim 1, wherein the butted end is formed by removing material in a wall thickness adjacent to the butted end.

8. The medical device of claim 1, wherein the opposite ends are butted and the butted ends have different wall thicknesses.

9. An implantable stent for use in a body lumen, comprising:
   a self-expanding body having a tubular shape with at least one butted end with material locally built up to extend radially inward increasing the wall thickness while maintaining a constant outside diameter along a length of the tubular shape;
   wherein the body includes a nickel-titanium alloy that is superelastic inside the body lumen; and
   a strut pattern formed from the tubular shape wherein the strut pattern includes a plurality of cylindrical rings generally aligned and interconnected by connecting links.

10. The stent of claim 9, wherein the body has two butted ends each having different lengths.

11. The stent of claim 9, wherein the butted end coincides with an end ring at an end of the stent.

12. The stent of claim 9, wherein the body has two butted ends and the butted ends are formed by removal of material in a section in between the butted ends.

13. The stent of claim 9, wherein a transition temperature of the nickel-titanium alloy is set at approximately 37 degrees C. and below approximately 37 degrees C.

14. A method for providing an implantable stent for use in a body lumen, comprising:
   providing a body having a tubular shape with opposite ends made from a nickel-titanium alloy that is superelastic inside the body lumen;
   forming a butted end at one of the ends by building up material radially inward thereby locally increasing the wall thickness while maintaining a constant outside diameter along a length of the tubular shape; and
   forming a strut pattern in the tubular shape wherein the strut pattern includes a plurality of cylindrical rings generally coaxially aligned and interconnected by connecting links.

15. The method of claim 14, wherein the step of forming a butted end includes thinning a wall thickness adjacent to the butted end by removing material.

16. The method of claim 14, wherein the step of forming a butted end includes thinning a wall thickness adjacent to the butted end by cold work.

17. The method of claim 14, wherein the step of forming a butted end includes thinning a wall thickness adjacent to the butted end by drawing.

18. The method of claim 14, wherein the method further comprises forming a second butted end at the opposite end.

19. The method of claim 14, wherein the step of forming a strut pattern includes laser cutting the pattern.

20. The method of claim 14, wherein the butted end is created by a material removal process selected from the group of processes consisting of: electric discharge machining, laser beam cutting, or chemical etching.

21. The method of claim 14, wherein the method further comprises providing a length of stock tubing, forming a plurality of butting along a length thereof, and cutting the stock tubing into multiple pieces.

22. An implantable stent for use in a body lumen, comprising:
   a tubular shape body having a mid-section and opposite ends including a nickel-titanium alloy that deforms superelastically when inside the body lumen;
   butting formed in an interior of the tubular shape body within the mid-section thereof with material built up radially inward thereby increasing the wall thickness locally while maintaining a constant outside diameter along a length of the tubular shape body; and
   a strut pattern formed from the tubular shape body wherein the strut pattern includes a plurality of cylindrical rings generally aligned and interconnected by connecting links.

23. The stent of claim 22, wherein the stent includes butting at an end of the tubular shape body.

24. The stent of claim 22, wherein the butting coincides with a ring of the strut pattern.

* * * * *